July 2, 1968 C. H. FISCHER Plant Pat. 2,817
GLADIOLUS PLANT
Filed Jan. 27, 1967
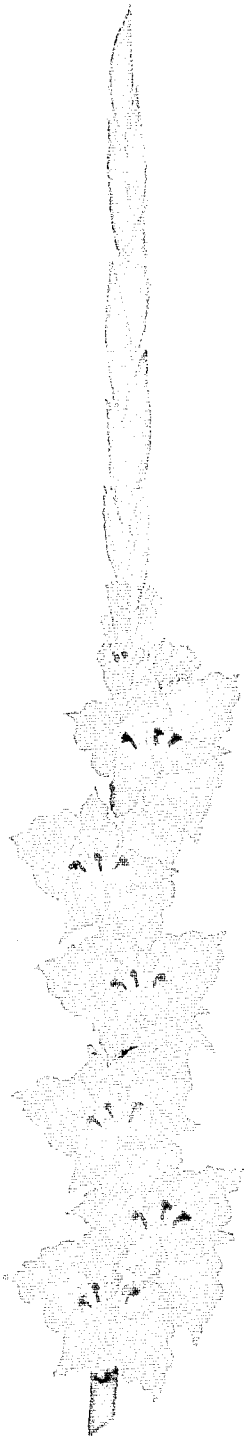
INVENTOR
Carl H. Fischer
By: Lamont Johnston
ATTORNEY United States Patent Office Plant Pat. 2,817
Patented July 2, 1968

2,817
GLADIOLUS PLANT

Carl H. Fischer, St. Charles, Minn., assignor to Selected Glads, Inc., New Albany, Ind., a corporation of Tennessee Filed Jan. 27, 1967, Ser. No. 612,282
1 Claim. (Cl. Plt.—85)

My invention relates to a new and improved variety of gladiolus and is notable particularly for its ability to grow and bloom well from small size bulbs, its prolific propagation and its ability to perform well in all parts of the United States. I have identified this new variety as seedling #113–60 in my breeding work.

To the best of my knowledge, this variety is the result of a cross between a seedling (unpatented) and Joyous (Plant Patent No. 1,832). The seedling was the seed parent and Joyous the pollen parent. Hand cross pollenization was done by me in my field at St. Charles, Minn., but no precaution was taken to prevent admixture by bees or insects.

This new variety has been asexually reproduced by me in Minnesota and California by natural increase from cormels through several generations and its characteristics have proven to be permanently fixed.

The illustration, made a part of this application, shows a single bloom spike, reduced in size, and is reasonably true to color. The illustration shows the form and placement of the florets on the spike.

In the following detailed description, color plate references are to "The Horticultural Colour Chart" by the British Colour Council. Where there are other references to color, the ordinary dictionary meanings of the terms are intended.

*The plant*

Growth: Vigorous; grows to 65 inches in height over-all. Good propagator.

Blooming: Blooms in 75 to 80 days from large bulbs in the North.

Stems: Diameter of the stems is ½ inch. Color of the stem above the bulb is streaked rose and white.

Foliage: Deep green, high broad and fan-shaped. Leaves are 1½ to 3¾ inches across. Plant foliage, excluding the flower spike, is 42 inches high.

Disease resistance: Excellent resistance to known gladiolus diseases.

Corms: Well-husked, round, plump and high-crowned. Husk is coarse, thick and red to purple in color. Color of flesh is Chrysanthemum Crimson $824/_3$.

*The flower*

Spike: Flowerhead is 28 inches high, with eighteen to twenty buds of which seven to eight open at one time.

Bud:

*Size.*—Opening buds are 3¼ inches long.

*Opening.*—Five to six show color at one time.

Flower:

*Arrangement.*—Florets are semi-formally placed on spike.

*Size.*—Individual florets are 5¼ to 5½ inches in diameter.

*Form.*—Ruffled, needlepointed and somewhat pointed, as a 6-pointed star.

*Keeping qualities.*—Excellent.

Petals:

*Shape.*—Ruffled; inner three petals are needlepointed as well. Outer three petals recurve considerably.

*Size.*—Upper petal is 2¼ inches across; lip is 1⅝ inches.

*Aspect.*—Firm substance.

*Fragrance.*—None.

*Color.*—Front of floret is Magenta Rose 27 shading from deepest color, 27 at petal edges and the center of the lip petal to $27/_3$ on the upper petal at the throat. Reverse of the floret is Tyrian Purple $727/_2$ shading to $727/_3$ at the base of the petals. The calyx is streaked with Tyrian Purple $727/_1$.

Reproductive organs:

*Stamens.*—Deep violet.

*Pistil.*—Magenta Rose $27/_2$.

*Comparisons*

My new variety resembles Joyous (Plant Patent No. 1,832) more than any other variety, but differs from it principally as follows:

(1) This new variety is lighter in color.

(2) It has a longer flowerhead and more buds.

(3) It is a more robust grower.

(4) It is more precocious; blooms better than small bulbs.

(5) This variety blooms earlier.

Having thus disclosed my invention, I claim:

1. The new and distinct variety of gladiolus plant, substantially as herein shown and described, characterized by its rugged plant, consistent performance, prolific propagation, ability to bloom well from small size bulbs and ability to perform well in all parts of the United States.

No references cited.

ROBERT E. BAGWILL, *Primary Examiner.*